US011202560B2

(12) United States Patent
Chang et al.

(10) Patent No.: US 11,202,560 B2
(45) Date of Patent: Dec. 21, 2021

(54) INTRAORAL SCANNER

(71) Applicant: MEDIT CORP., Seoul (KR)

(72) Inventors: Min Ho Chang, Seoul (KR); Byung Ho Song, Goyang-si (KR); Mooncheol Jeong, Seoul (KR); Eungil Cho, Gunpo-si (KR); Seungjin Lee, Gunpo-si (KR)

(73) Assignee: MEDIT CORP., Seoul (KR)

( * ) Notice: Subject to any disclaimer, the term of this patent is extended or adjusted under 35 U.S.C. 154(b) by 0 days.

(21) Appl. No.: 16/699,290

(22) Filed: Nov. 29, 2019

(65) Prior Publication Data

US 2020/0170497 A1 Jun. 4, 2020

(30) Foreign Application Priority Data

Nov. 29, 2018 (KR) .................. 10-2018-0150535
Nov. 26, 2019 (KR) .................. 10-2019-0152822

(51) Int. Cl.
*H04N 7/18* (2006.01)
*A61B 1/24* (2006.01)
(Continued)

(52) U.S. Cl.
CPC ................. *A61B 1/24* (2013.01); *A61B 1/05* (2013.01); *A61B 1/0646* (2013.01);
(Continued)

(58) Field of Classification Search
CPC .... A61B 1/04; A61B 1/24; A61B 1/05; A61B 1/0646; A61B 1/0676; A61B 1/127;
(Continued)

(56) References Cited

U.S. PATENT DOCUMENTS 5,897,509 A * 4/1999 Toda .................. A61B 1/24
600/589
5,993,209 A * 11/1999 Matoba ................ A61C 19/043
433/72
(Continued)

FOREIGN PATENT DOCUMENTS

CN 108478177 A 9/2018
KR 10-1648970 B1 8/2016
(Continued)

OTHER PUBLICATIONS

Korean Office Action for related KR Application No. 10-2019-0152822 dated Feb. 19, 2021 from Korean Intellectual Property Office.
Dentcore Inc., "How to Calibrate the Medit 1500", URL:https://www.youtube.com/watch?v=TBmuJOSPBSg&ab_channel=DentCoreInc, Sep. 5, 2018.

*Primary Examiner* — Trang U Tran
(74) *Attorney, Agent, or Firm* — Paratus Law Group, PLLC

(57) ABSTRACT

Disclosed is an intraoral scanner, including: a main body having a light projector, a camera lens, and an intake fan disposed therein; a probe tip mount disposed at the front end of the main body, and formed with a light gate; and a probe tip having the probe tip mount inserted into the rear end portion thereof, and having a reflective member for reflecting the light irradiated from the light projector through the light gate into an oral cavity and reflecting the light reflected from the interior of the oral cavity to the camera lens through the light gate disposed on the front end portion thereof. The probe tip mount is further formed with a guide hole for guiding the air flowing into the main body by the intake fan to the reflective member.

10 Claims, 13 Drawing Sheets

(51) Int. Cl.
*A61B 1/12* (2006.01)
*A61B 1/05* (2006.01)
*A61B 1/06* (2006.01)
*H04N 5/225* (2006.01)
*H04N 5/235* (2006.01)

(52) U.S. Cl.
CPC ............ *A61B 1/0676* (2013.01); *A61B 1/127* (2013.01); *H04N 5/2254* (2013.01); *H04N 5/2354* (2013.01); *H04N 2005/2255* (2013.01)

(58) Field of Classification Search
CPC ...... H04N 7/18; H04N 5/2254; H04N 5/2354; H04N 2005/2255
USPC ...................................................... 348/66, 77
See application file for complete search history.

(56) References Cited

U.S. PATENT DOCUMENTS

| | | | |
|---|---|---|---|
| 7,494,338 B2* | 2/2009 | Durbin | A61C 9/00 433/29 |
| 2010/0238279 A1* | 9/2010 | Thoms | A61B 1/247 348/77 |
| 2010/0268069 A1* | 10/2010 | Liang | A61B 5/0088 600/425 |
| 2018/0333232 A1* | 11/2018 | Lee | G01B 21/042 |
| 2019/0247163 A1* | 8/2019 | Wu | A61B 5/4547 |

FOREIGN PATENT DOCUMENTS

| | | |
|---|---|---|
| KR | 10-1844746 B1 | 4/2018 |
| KR | 10-1874547 B1 | 7/2018 |

\* cited by examiner

[FIG. 1]
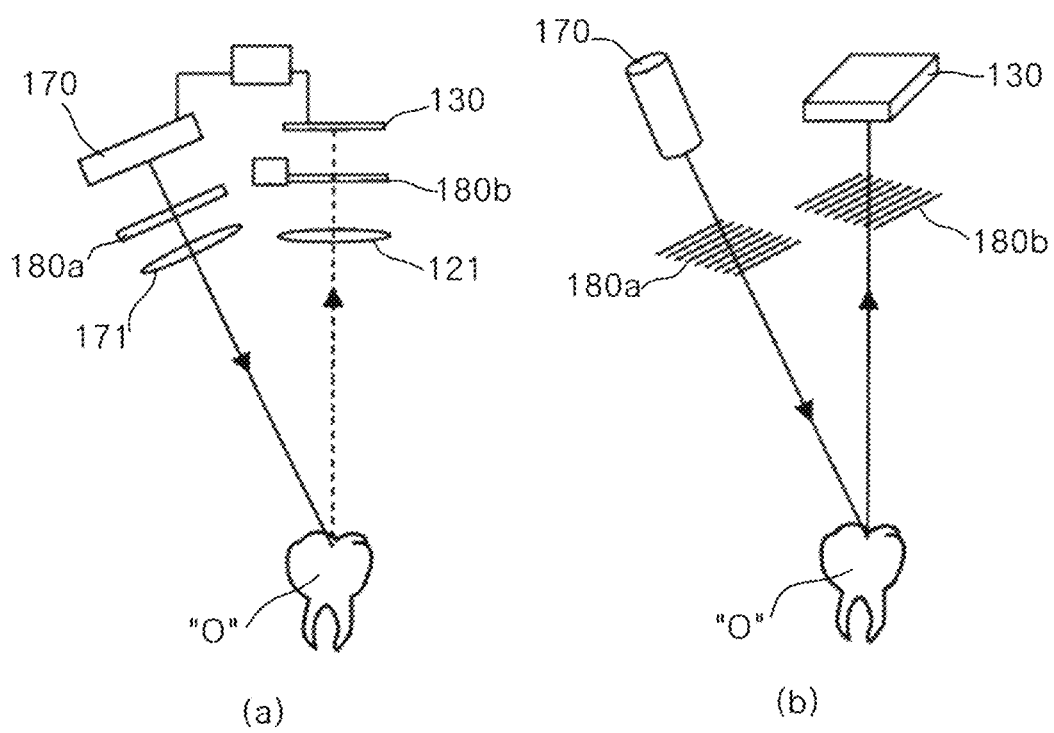
(a)　　　　　　　　　(b)

[FIG. 2]
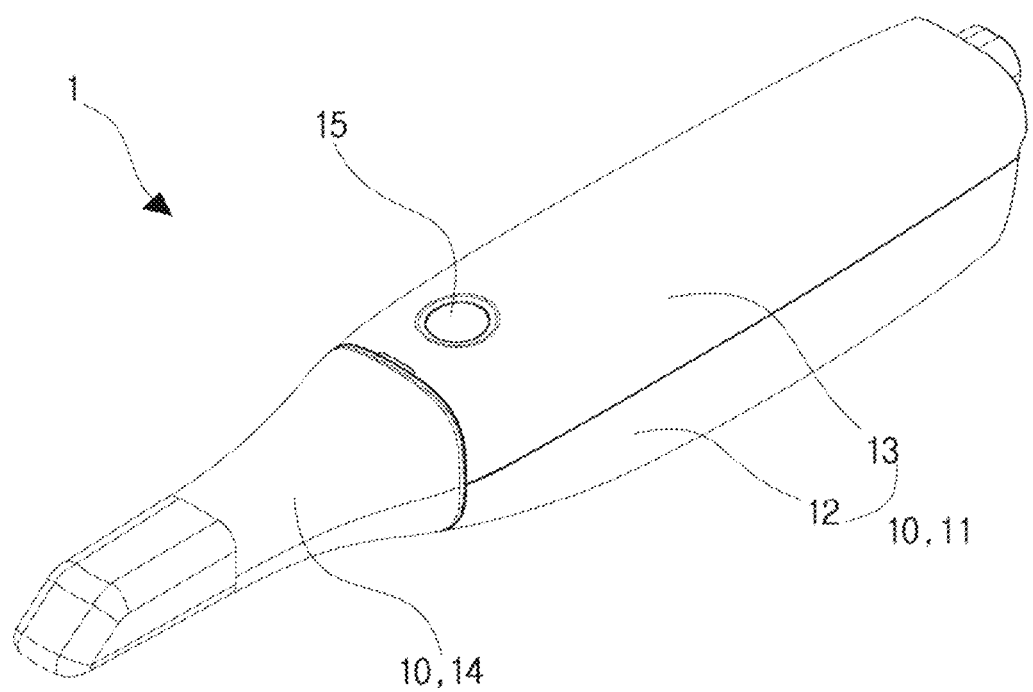

[FIG. 3]
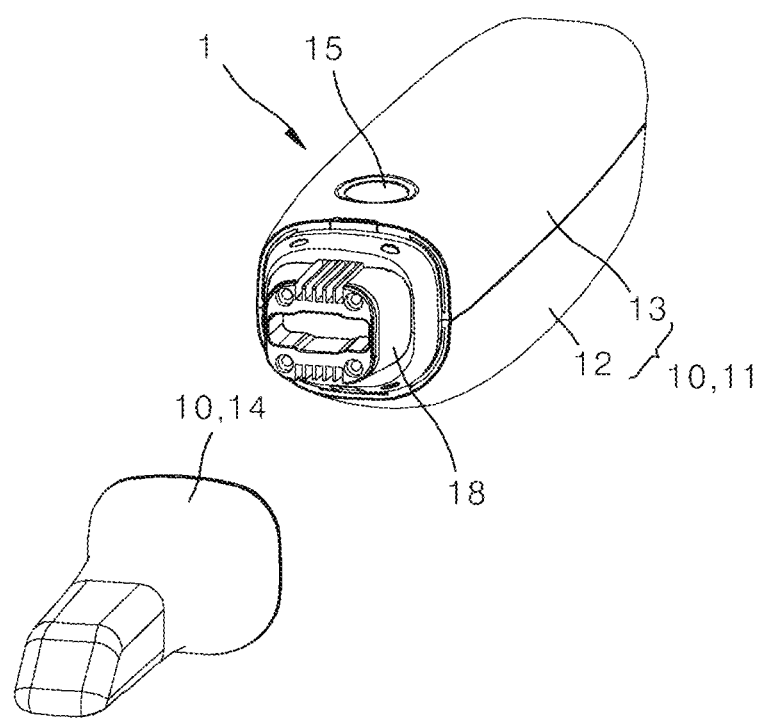

[FIG. 4]
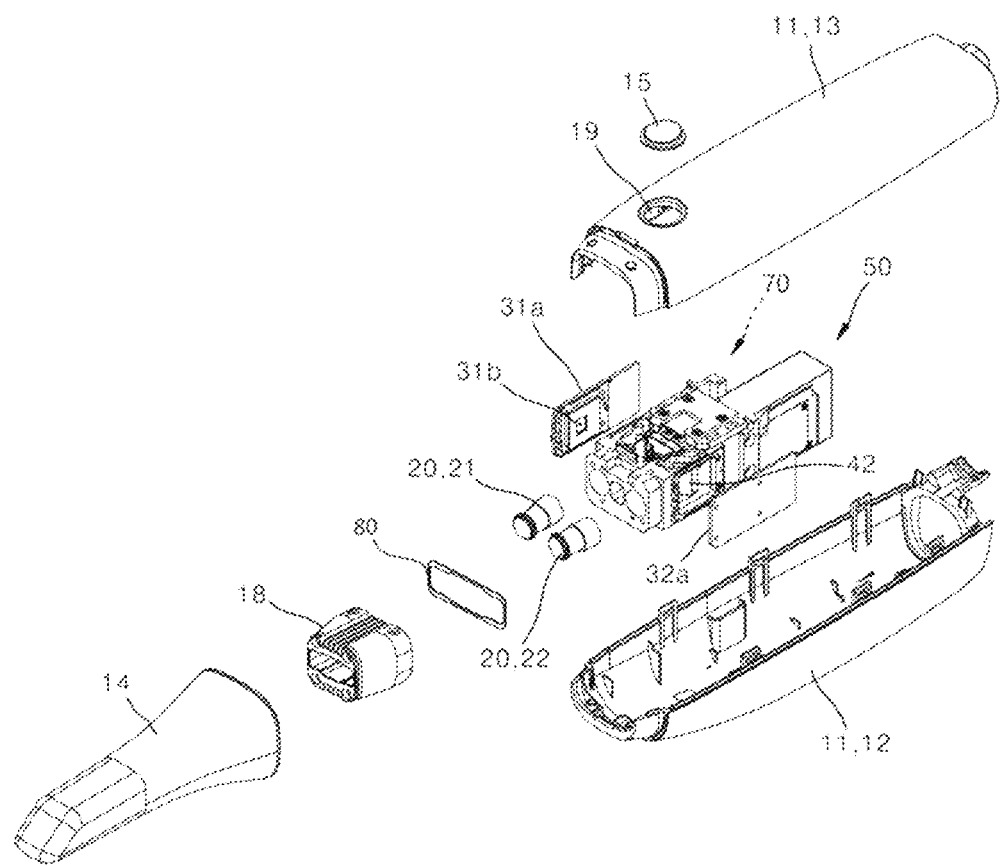

[FIG. 5]
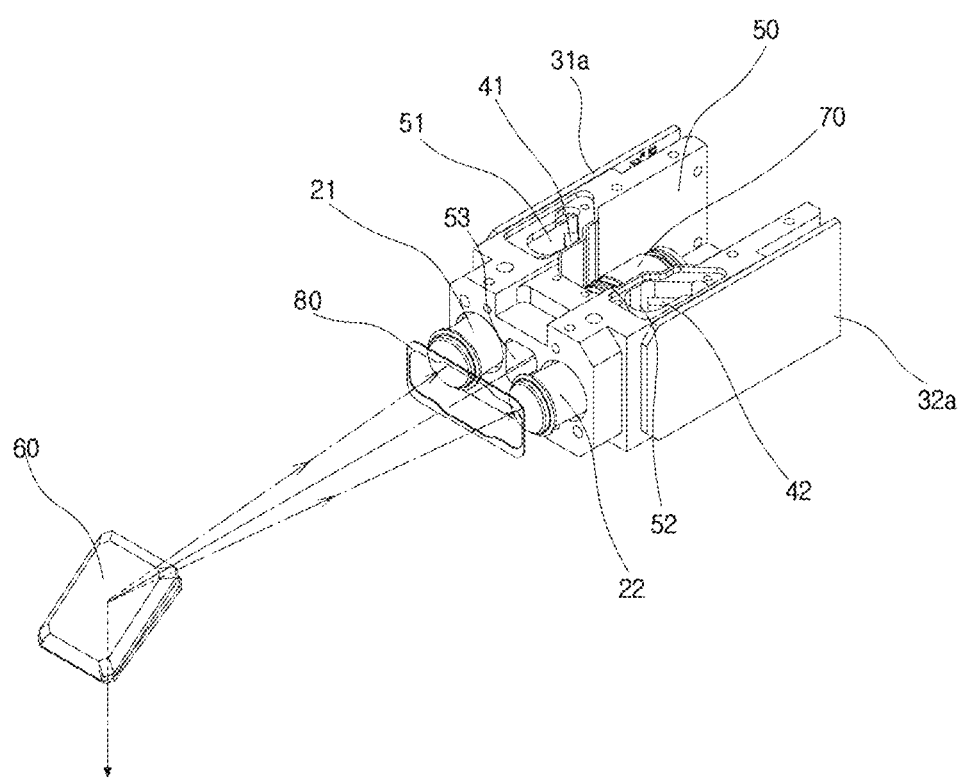

[FIG. 6]
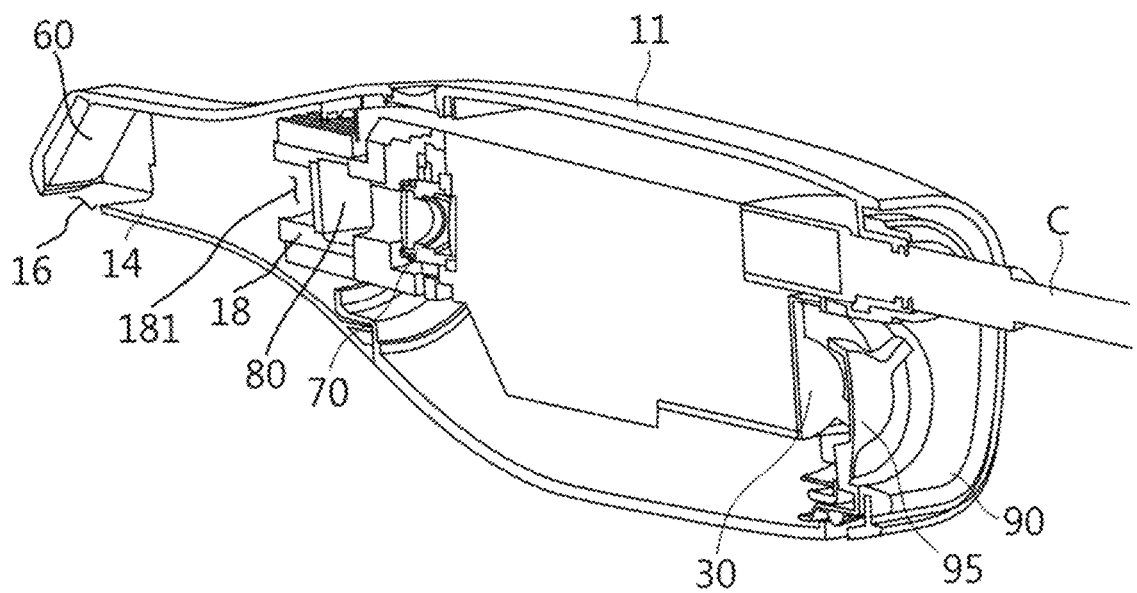
[FIG. 7]
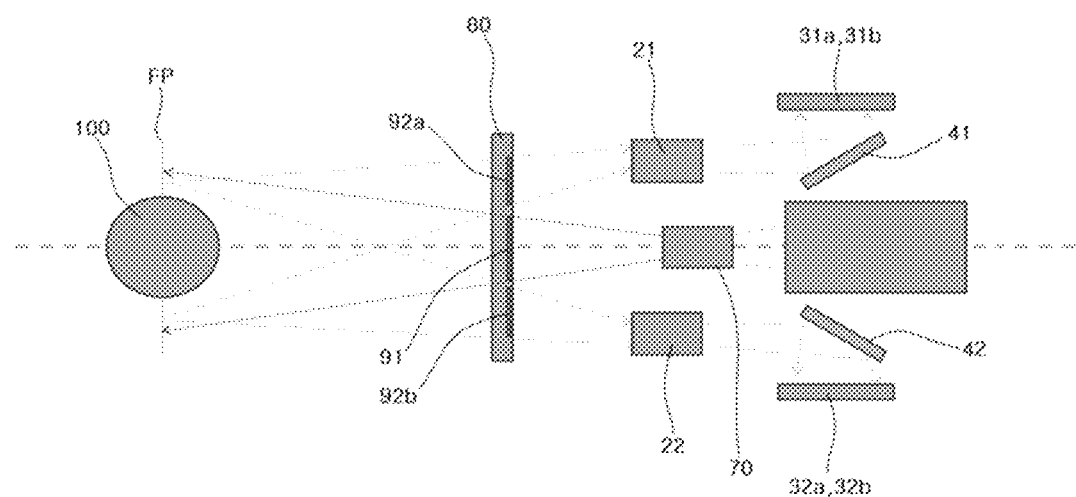

[FIG. 8]
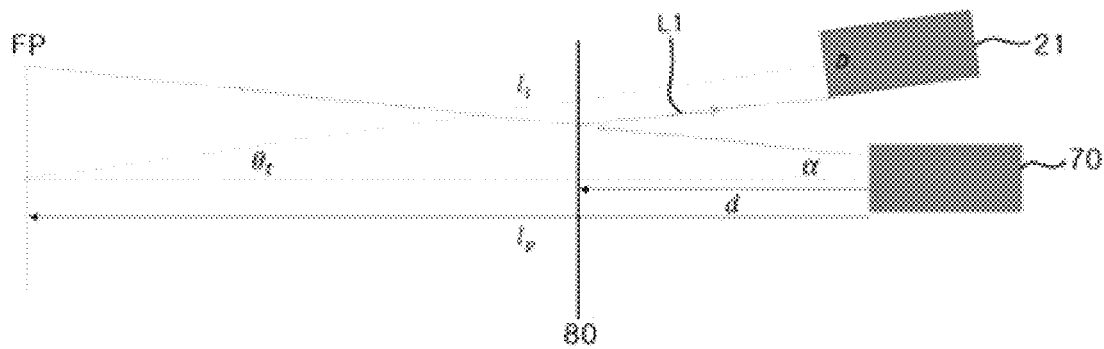
[FIG. 9]
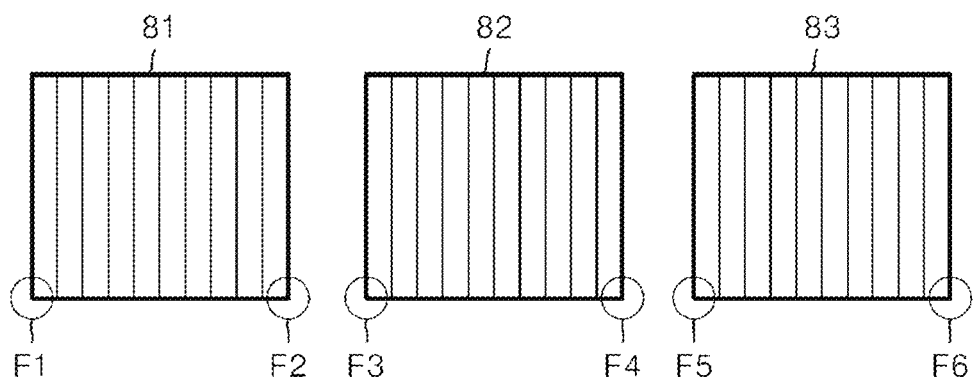
(a)
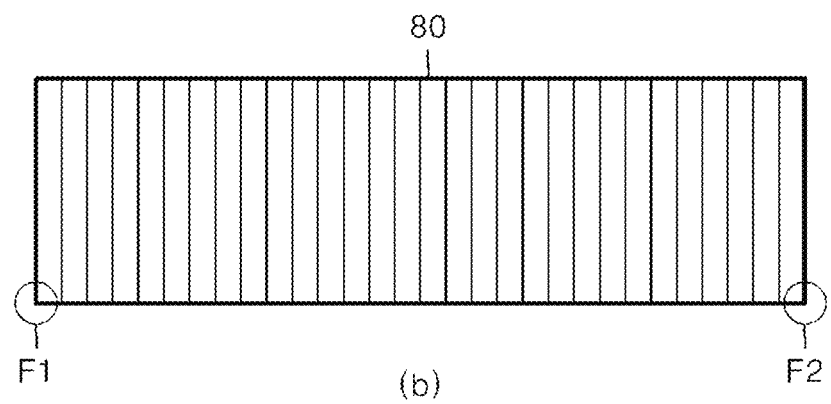
(b)

[FIG. 10]
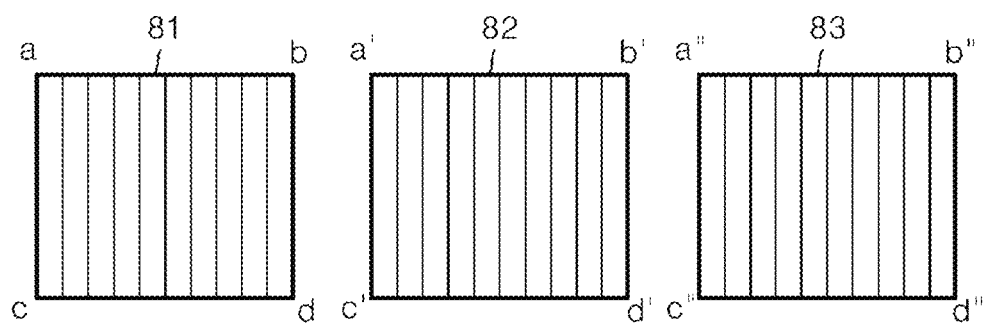
(a)
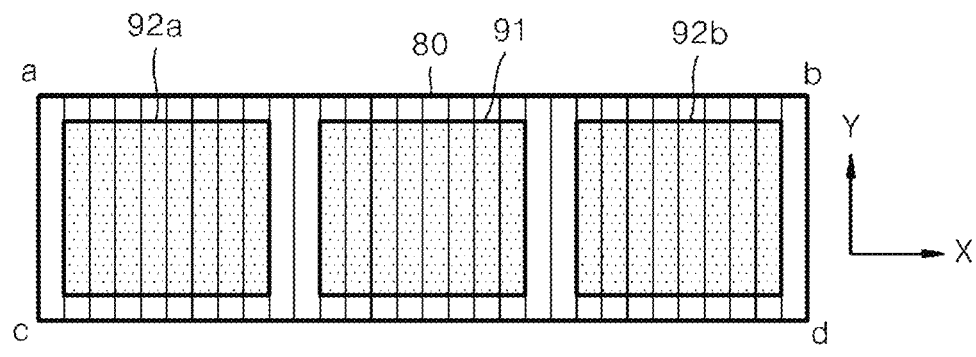
(b)

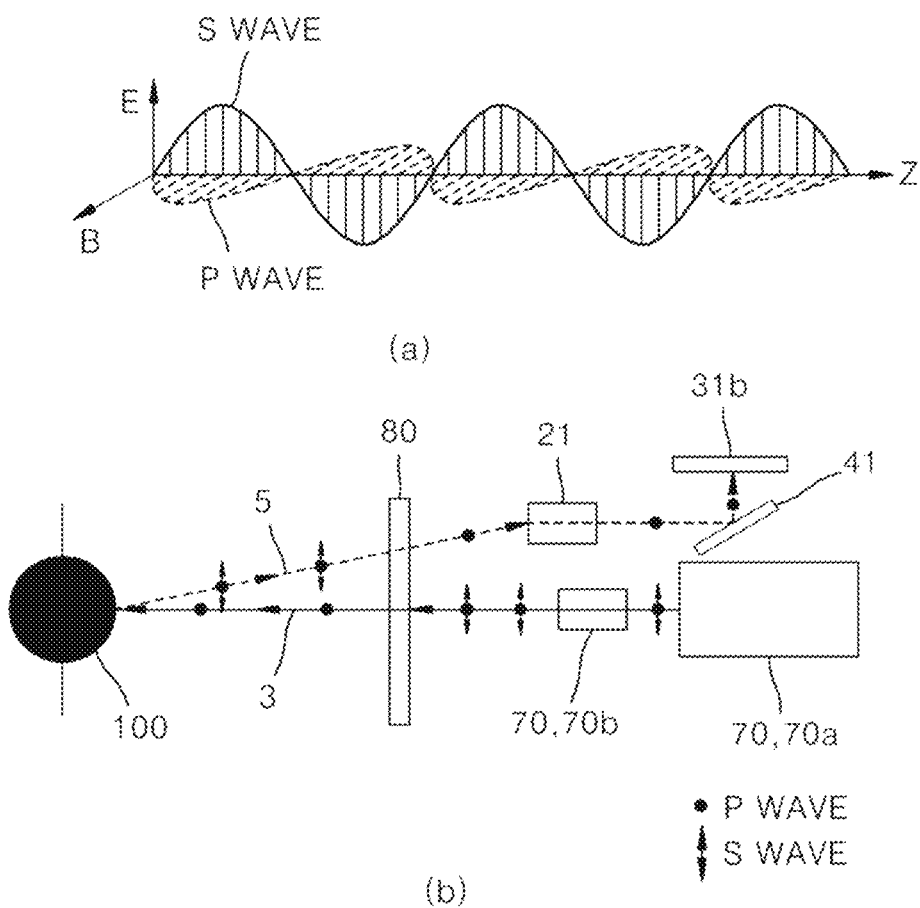
[FIG. 11]

[FIG. 12]
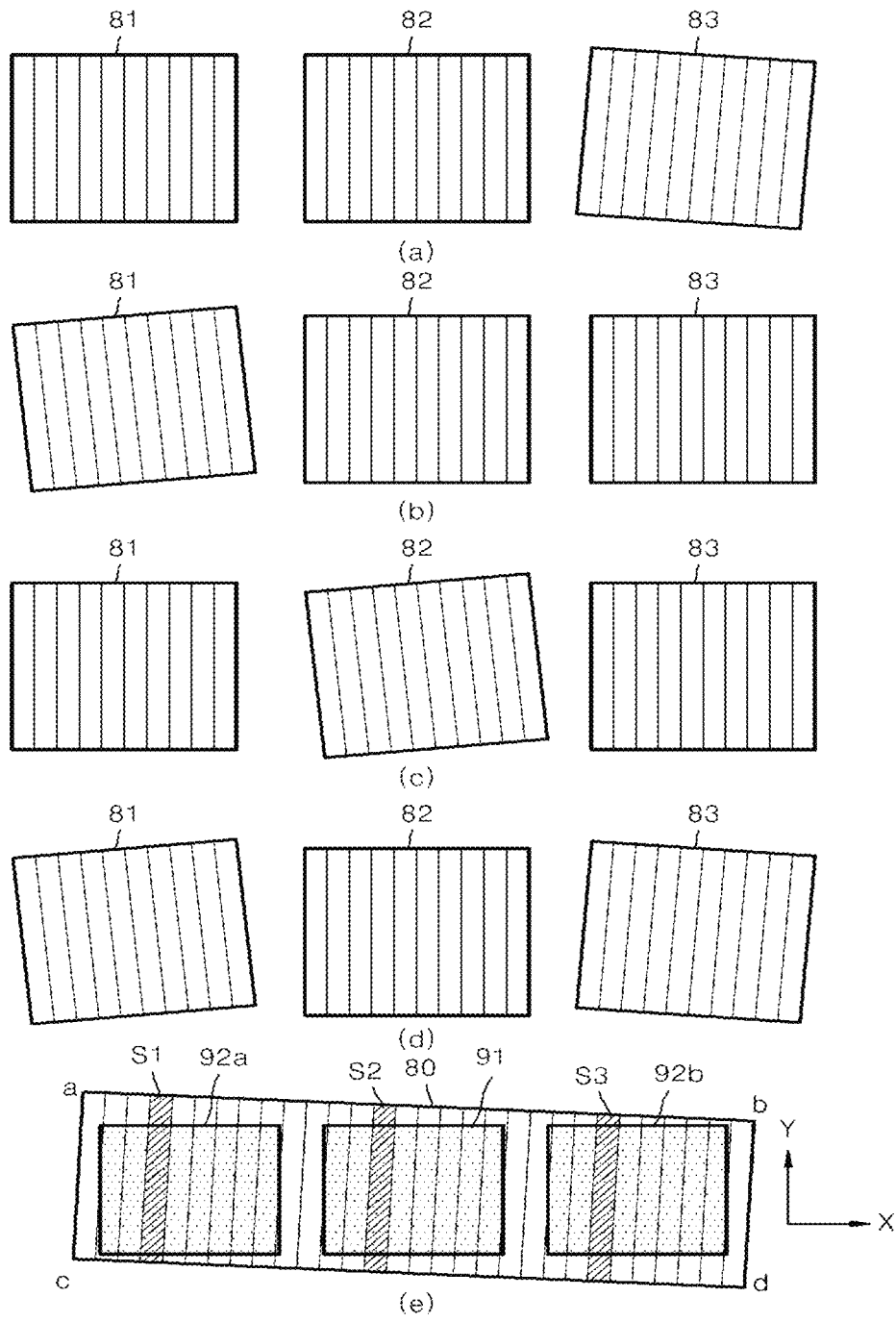

[FIG. 13]
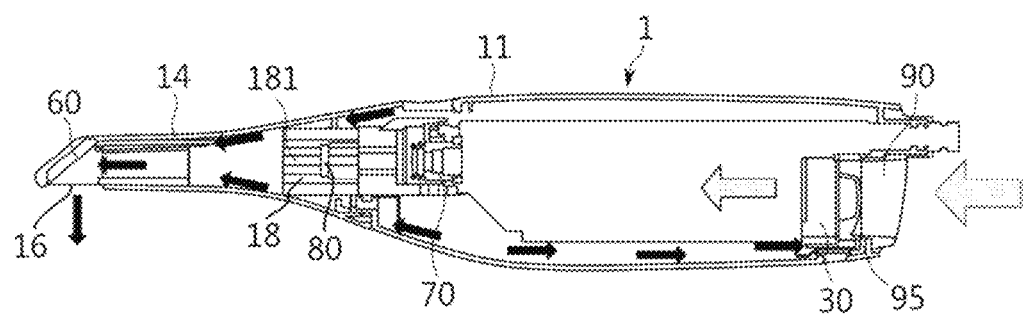

[FIG. 14]
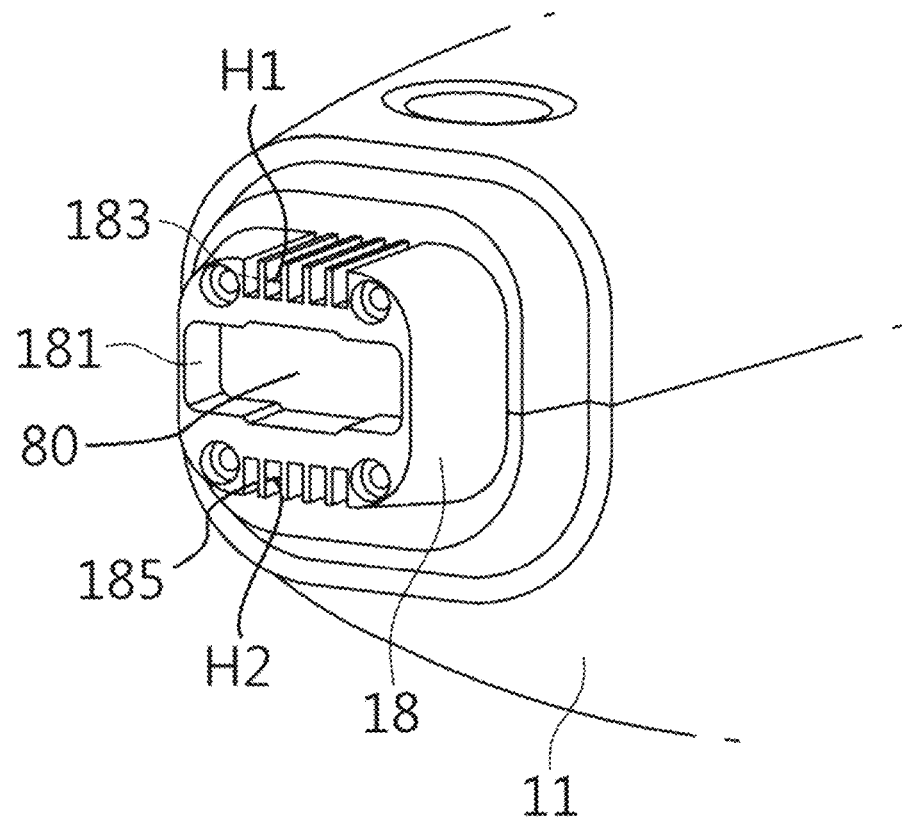

[FIG. 15]
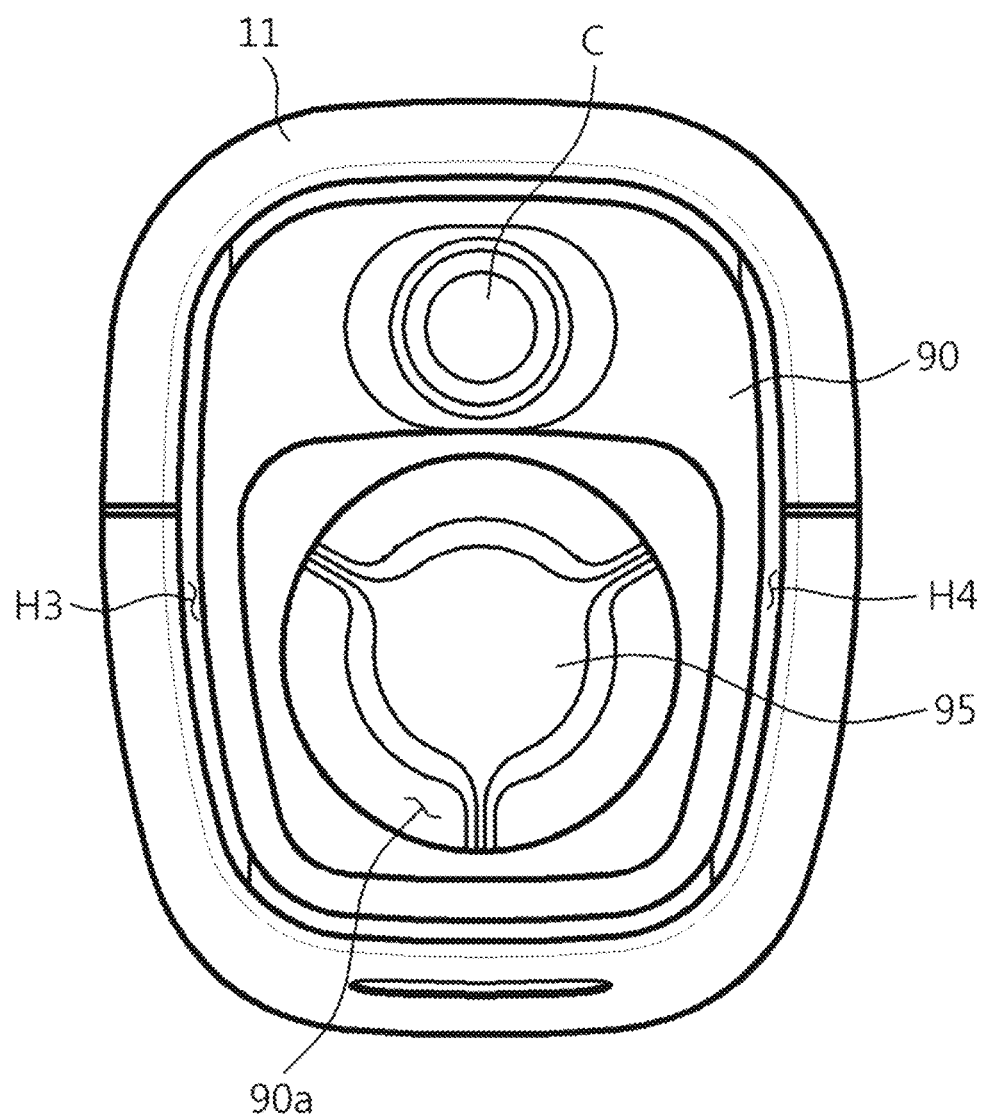

INTRAORAL SCANNER

CROSS-REFERENCE TO RELATED APPLICATIONS

This application claims priority to Korean Patent Application No. 10-2018-0150535, filed on Nov. 29, 2018 and Korean Patent Application No. 10-2019-0152822, filed on Nov. 26, 2019 in the Korean Intellectual Property Office, which are all hereby incorporated by reference in their entirety.

BACKGROUND

The present disclosure relates to an intraoral scanner, and more particularly, to an intraoral scanner, which may irradiate light into an oral cavity and then scan the intraoral structure through the image processing of light reflected from the interior of the oral cavity.

In general, a dental clinic or the like performs treatment and care for a patient's damaged tooth through the impression taking of producing a plaster model of the patient's teeth.

As described above, in the impression taking of producing the plaster model, there may occur problems such as consumption of a material and cross infection, the possibility of breakage and the preservation problem of the produced model, and the like.

In particular, in the case of manually taking the impression of the patient's damaged tooth by using the impression material, the degree of error in the three-dimensional information of the produced prosthesis may not be confirmed, such that there is a problem in that the actually produced prosthesis does not match in the patient's oral cavity.

Therefore, recently, a three-dimensional intraoral scanner capable of obtaining accurate three-dimensional information on the damaged tooth without using an impression material to produce a prosthesis having the accurate dimension has been widely used.

Korean Patent No. 10-1874547 (issued date: Jul. 4, 2018) (hereinafter referred to as 'related art') discloses 'the three-dimensional intraoral scanner,' which may dispose the light path changing part at the front end of the imaging sensor, thereby increasing the degree of freedom of the placement of the imaging board on which the imaging sensor is disposed, and maximizing the utilization of the internal space.

The related art includes a light projector for generating light and a reflective mirror for reflecting the light irradiated from the light projector into the oral cavity and also reflecting the light reflected from the interior of the oral cavity to a lens.

In the related art, the light reflected from the interior of the oral cavity to the lens through the reflective mirror passes through the lens, and then is input to the imaging sensor through the light path changing part, and the imaging board installed with the imaging sensor may perform the image processing for the light input to the imaging sensor to scan the interior of the oral cavity.

However, in the related art, there has been a problem in that condensation occurs on the reflective mirror (hereinafter, referred to as 'reflective member') by the water vapor in the oral cavity generated in the patient's respiratory process due to the nature of the intraoral scanner to enter the patient's oral cavity, thereby disturbing the scanning of the oral cavity.

Further, in the related art, there has been also a problem that it is not possible to obtain the accurate three-dimensional data due to the noise of the light transmitted to and reflected from the teeth because the light irradiated into the oral cavity is not only reflected from the surface of the teeth, but also transmitted to and reflected from the teeth.

FIG. 1 is a schematic diagram of obtaining three-dimensional information by using an intraoral scanner including a polarization filter according to the related art.

Further, in order to form a three-dimensional scanning model for the teeth in the oral cavity by using the intraoral scanner, as illustrated in FIG. 1A, there is taken a method of projecting the structured light onto the teeth, which is the measurement object (O), and obtaining the light reflected therefrom to obtain the three-dimensional data therefrom.

That is, the light generated from a light generating part 170 transmits a projection lens 171 to be reflected from the interior of the oral cavity including the teeth, which is the measurement object (O) and then is incident therein through a camera lens 121 to obtain three-dimensional data through the imaging sensor 130.

In order to obtain precise surface data about the teeth in this method, it is important to accurately project the projected structured light onto the teeth, which is the surface of the measurement object (O), and to obtain it. However, in the related art, there has been also a problem that it is not possible to obtain the accurate three-dimensional data due to the noise of the light transmitted to and reflected from the teeth because the light irradiated into the oral cavity is not only reflected from the surface of the teeth, but also transmitted to and reflected from the teeth.

In order to solve it, methods of obtaining the light reflected only from the surface of the internal reflective material of the measurement object by using optical wave characteristics (for example, a method of using polarization filters 180a, 180b) are researched and developed, but it is difficult to apply it due to the adjustment of the precise optical axis and the surface reflection problem of the polarization filters 180a, 180b themselves so that there is no loss of three-dimensional data even in the case of using the polarization filters 180a, 180b.

Further, even in the case of applying the polarization filters 180a, 180b, as illustrated in FIG. 1B, the first polarization filter 180a should be provided in the projecting path before the light from the light generating part 170 is projected to the measurement object (O), and the second polarization filter 180b should be provided in the incident path before it is reflected from the measurement object (O) to be incident to the imaging sensor 130, which means that at least two polarization filters 180a, 180b should be provided in the case of a single camera, and furthermore, means that at least three polarization filters should be provided in the case of applying a stereo vision method, thereby leading to a problem that it is very difficult to conduct the slim design of the overall product.

RELATED ART DOCUMENT

Patent Document (Patent Document 1) Korean Patent No. 10-1874547 (Issued date: Jul. 4, 2018)

SUMMARY

An object of the present disclosure is to provide an intraoral scanner, which may send a portion of the air sucked into an intraoral scanner and then heated by the heat inside the intraoral scanner to a reflective member, thereby preventing the condensation phenomenon of the reflective member.

Another object of the present disclosure is to provide an intraoral scanner, which may smoothly discharge the remainder of the heated air to the outside of the intraoral scanner.

Still another object of the present disclosure is to provide an intraoral scanner, which may remove the noise of the light reflected from the interior of the teeth rather than the surface of the teeth through a single polarization filter to obtain the accurate image.

The objects of the present disclosure are not limited to the above-mentioned objects, and other objects not mentioned will be clearly understood by those skilled in the art from the following description.

For achieving the objects, an intraoral scanner according to the present disclosure is composed of a main body, a probe tip mount, and a probe tip. A light projector, a camera lens, and an intake fan are disposed inside the main body. The probe tip mount is disposed at the front end of the main body. The probe tip mount is formed with a light gate. The probe tip mount is inserted into the rear end portion of the probe tip. A reflective member is disposed on the front end portion of the probe tip. The reflective member reflects the light irradiated from the light projector through the light gate into an oral cavity. The reflective member reflects the light reflected from the interior of the oral cavity to the camera lens through the light gate. The probe tip mount is further formed with a guide hole. The guide hole guides the air flowing into the main body by the intake fan to the reflective member.

The guide hole may be formed to be recessed in the outer circumferential surface of the probe tip mount.

The guide hole may be composed of a first guide hole and a second guide hole. The first guide hole may be formed at one side of the outer circumferential surface of the probe tip mount. The second guide hole may be formed at the other side of the outer circumferential surface of the probe tip mount.

The probe tip mount may be further formed with a plurality of first partition walls and a plurality of second partition walls. The plurality of first partition walls may partition the first guide hole into a plurality of first guide holes. The plurality of second partition walls may partition the second guide hole into a plurality of second guide holes.

The probe tip mount may be made of a heat dissipation material.

The intraoral scanner according to the present disclosure may further constitute a back cover. The back cover may be disposed at the rear of the main body. The back cover may be formed with an intake port. The rim of the back cover may be formed with an air discharge hole. The air discharge hole may discharge the air flowing into the main body through the intake port.

The air discharge hole may be composed of a first air discharge hole and a second air discharge hole. The first air discharge hole may be formed at one side of the rim of the back cover. The second air discharge hole may be formed at the other side of the rim of the back cover.

A single polarization filter may be further installed inside the probe tip mount. The single polarization filter may be disposed at the light gate.

The single polarization filter may be disposed to be spaced forward at a setting distance apart from the light projector and the camera lens.

The camera lens may be provided as a plurality of camera lenses.

The intraoral scanner according to the present disclosure may further constitute a main mount. The main mount may be disposed in the main body. The main mount may have the plurality of camera lenses and the light projector mounted thereon. The main mount may be formed with a plurality of incident light path parts and an emitted light path part. The plurality of incident light path parts may provide the path of the light incident to the plurality of camera lenses. The emitted light path part may provide the path of the light irradiated from the light projector.

The setting distance may satisfy the following equation.

$$d < \frac{\left(l_i \ominus_i - \frac{D}{2}\right)}{2\tan a} + \frac{(l_p - l_i)}{2} \quad \text{Equation}$$

where d refers to the setting distance, $l_p$ refers to the distance from the light projector to a measurement object, $l_t$ refers to the distance from the camera lens to the measurement object, $\ominus_i$ refers to the triangulation angle, D refers to the diameter of the camera lens, and $\alpha$ refers to the angle of view of the light irradiated from the light projector.

The probe tip mount may dissipate the heat generated in the main mount to the outside.

The specific contents of other embodiments are included in the detailed description and the drawings.

Since the intraoral scanner according to the present disclosure forms the guide hole for guiding the air flowing into the main body by the intake fan to the reflective member on the probe tip mount, a portion of the air heated in the main body may be moved to the reflective member through the guide hole, thereby preventing the condensation phenomenon of the reflective member.

Further, it is possible to form the air discharge hole through which the remainder of the heated air is discharged in the rim of the back cover, thereby discharging the remainder of the heated air through the air discharge hole.

Further, since the single polarization filter is disposed at the front of the light projector and the camera lens, it is possible to remove the light transmitted to and then reflected from the teeth from the light reflected from the interior of the oral cavity to be incident into the intraoral scanner, thereby securing the accurate image data.

The effects of the present disclosure are not limited to the effects mentioned above, and other effects not mentioned will be clearly understood by those skilled in the art from the description of the claims.

BRIEF DESCRIPTION OF THE DRAWINGS

FIG. 1 is a schematic diagram of obtaining three-dimensional information using an intraoral scanner including a polarization filter according to the related art.

FIG. 2 is a perspective diagram illustrating an intraoral scanner according to an embodiment of the present disclosure.

FIG. 3 is a perspective diagram illustrating a state where a probe tip has been separated from a main body illustrated in FIG. 2.

FIG. 4 is an exploded perspective diagram of FIG. 2.

FIG. 5 is a diagram illustrating the moving path of the light in the intraoral scanner according to an embodiment of the present disclosure.

FIG. 6 is a side cutout perspective diagram of the intraoral scanner according to an embodiment of the present disclosure.

FIG. 7 is a schematic plane diagram for explaining the position design of a single polarization filter illustrated in FIGS. 4 to 6.

FIG. 8 is a schematic plane diagram illustrating a first angle of view, a second angle of view, and a triangulation angle illustrated in FIG. 7.

FIGS. 9 to 12 are diagrams for explaining the advantage of the single polarization filter.

FIG. 13 is a diagram illustrating the moving path of the air sucked into the intraoral scanner according to an embodiment of the present disclosure.

FIG. 14 is an enlarged diagram of a probe tip mount illustrated in FIG. 3.

FIG. 15 is a diagram illustrating a back cover installed at the rear of the main body.

DETAILED DESCRIPTION

Hereinafter, an intraoral scanner according to an embodiment of the present disclosure will be described with reference to the drawings.

FIG. 2 is a perspective diagram illustrating the intraoral scanner according to an embodiment of the present disclosure.

Referring to FIG. 2, an intraoral scanner 1 according to an embodiment of the present disclosure may irradiate irradiated light to a structure in an oral cavity, and obtain an optical image of the surface of the structure in the oral cavity from which the irradiated light has been reflected.

The intraoral scanner 1 may include a case 10. The case 10 may form the appearance of the intraoral scanner 1. The front portion of the case 10 may be inserted into and withdrawn from the patient's oral cavity. The case 10 may be formed lengthily back and forth in order to enable the insertion into and the withdrawal from the oral cavity.

The longitudinal section of the case 10 may be formed in a substantially square shape. The four corners on the square shape may be rounded to be convex outward.

The case 10 may include a main body 11 and a probe tip 14. The main body 11 may be disposed at the rear of the probe tip 14, and the probe tip 14 may be disposed at the front of the main body 11.

The circumference of the main body 11 may be formed in the size that may be gripped by the user. In order to facilitate the insertion into the patient's oral cavity, the circumference of the front portion of the probe tip 14 is preferably formed smaller than the circumference of the rear portion of the probe tip 14.

The main body 11 may include an upper case 13 and a lower case 12.

The upper case 13 may be provided with a user input part 15. The user input part 15 is for operating the intraoral scanner 1, and may include a sensing device, a button, a keypad, a touch pad, and the like such as pressure or illuminance. If the user operates the user input part 15, the intraoral scanner 1 may be operated. The user input part 15 may be installed in an input part installation hole 19 (see FIG. 4) formed in the upper case 13.

The lower case 12 may be formed to have a concave upper side and a convex lower side. The upper case 13 may be formed to have a convex upper side and a concave lower side. In the case of a state where the lower case 12 and the upper case 13 have been coupled to each other, the main body 11 may form an internal space.

A main mount 50, a light projector 70, a camera lens 20, imaging boards 31a, 32a, an intake fan 30, and the like to be described later, may be installed in the internal space of the main body 11.

FIG. 3 is a perspective diagram illustrating a state where a probe tip has been separated from the main body illustrated in FIG. 2.

Referring to FIG. 3, a probe tip mount 18 may be disposed to be protruded forward from the front end of the main body 11. The rear end portion of the probe tip mount 18 may be disposed to be inserted into the internal space of the main body 11, and the front end portion of the probe tip mount 18 may be disposed to be protruded forward from the main body 11.

The probe tip 14 may be mounted to the probe tip mount 18. The rear end portion of the probe tip 14 may be covered on the outer circumferential surface of the probe tip mount 18. The probe tip mount 18 may be disposed to be inserted into the rear end portion of the probe tip 14.

A plurality of coupling ribs (not illustrated) may be formed to be protruded from the inner circumferential surface of the rear end portion of the probe tip 14. In the case of a state where the probe tip mount 18 has been inserted into the rear end portion of the probe tip 14, the plurality of coupling ribs may be in close contact with the outer circumferential surface of the probe tip mount 18, thereby maintaining a state where the probe tip 14 has been mounted to the probe tip mount 18. As described above, since the probe tip 14 is mounted to the probe tip mount 18 to be easily separable and connectable, it is possible to be easily replaced with the probe tip 14 suitable for the size and use of the patient's oral cavity.

FIG. 4 is an exploded perspective diagram of FIG. 2, FIG. 5 is a diagram illustrating the moving path of the light in the intraoral scanner according to an embodiment of the present disclosure, and FIG. 6 is a side cutout perspective diagram of the intraoral scanner according to an embodiment of the present disclosure.

Referring to FIGS. 4 to 6, at least one camera lens 20 may be disposed inside the main body 11.

Although not illustrated in the drawings, at least one camera lens 20 may also be provided as a single camera lens 20 or may also be provided as a plurality of camera lenses 20.

Further, at least one camera lens 20 may also be provided as a pair of camera lenses 20, as illustrated in FIG. 4. That is, at least one camera lens 20 may include a first camera lens 21 disposed at one side of the main body 11 and a second camera lens 22 disposed at the other side of the main body 11.

The first camera lens 21 and the second camera lens 22 may be disposed to be spaced apart from each other in the main body 11 in the width direction of the main body 11, thereby passing through the light incident from one end portion of the probe tip 14 in different paths, respectively.

Here, the term 'light' means light in a visible light area that may be seen by the human eye in a broad sense, but may be a concept that includes all of the light in an infrared or ultraviolet area that may be observed by using a special optical device, and may refer to the figure of the interior of the patient's oral cavity to be measured (hereinafter, referred to as 'image') in a narrow sense.

Therefore, the probe tip 14 may be formed with an opening 16 that is opened so that the image flows into the interior thereof in the form of light through one end portion thereof. The opening 16 may be an inlet through which the light outside the probe tip 14 flows into the probe tip 14. The light incident through the opening 16 is transmitted to each of the first camera lens 21 and the second camera lens 22 while forming different light paths, respectively. The image of the light having transmitted the first camera lens 21 and the second camera lens 22 may be photographed through the imaging sensors 31b, 32b provided on the imaging boards 31a, 32a to be described later.

Here, the image may be secured with two image data at the same time, such that if it is known the spacing distance between the first camera lens 21 and the second camera lens 22, and the focal distance of the object point photographed through the first camera lens 21 and the second camera lens 22, the three-dimensional image data of the image may be secured.

Although not specifically illustrated, each of the first camera lens 21 and the second camera lens 22 may include at least two transmission lenses capable of adjusting the focus of the image in the oral cavity.

The intraoral scanner 1 according to an embodiment of the present disclosure may further include a first imaging board 31a having a first imaging sensor 31b for sensing the light having passed through the first camera lens 21, and a second imaging board 32a having a second imaging sensor (not illustrated) for sensing the light having passed through the second camera lens 22. Although the second imaging sensor is not illustrated in FIG. 4, the second imaging sensor, which is the same as the first imaging sensor 31b, may be disposed on the surface of the second imaging board 32a facing the first imaging board 31a.

The first imaging board 31a may perform the imaging processing for the light sensed by the first imaging sensor 31b. The second imaging board 32a may perform the imaging processing for the light sensed by the second imaging sensor.

An opening 16 may be formed in the front end portion of the probe tip 14. The opening 16 may be formed to be opened in one side direction orthogonal to the longitudinal direction of the probe tip 14.

The probe tip 14 may be formed with the internal space lengthened back and forth. The internal space of the probe tip 14 may extend from the rear end of the probe tip 14 to the opening 16. The internal space of the probe tip 14 may guide the light emitted from the interior of the main body 11 into the oral cavity through the opening 16, and guide the light incident into the main body 11 from the interior of the oral cavity through the opening 16.

The light emitted from the interior of the main body 11 into the oral cavity through the opening 16 (hereinafter, referred to as 'emitted light') may mean the irradiation light irradiated from the light projector 70 to be described later. Further, the light incident to the main body 11 from the interior of the oral cavity through the opening 16 (hereinafter, referred to as 'incident light') may mean the image, which is the figure of the interior of the patient's oral cavity.

Further, a reflective member 60 may be disposed at the front end portion of the probe tip 14. The reflective member 60 may be disposed inside the front end of the probe tip 14. The front end of the probe tip 14 may be formed to be inclined, and the reflective member 60 may be disposed to be inclined inside the front end of the probe tip 14.

The reflective member 60 may be a mirror. However, the reflective member 60 is not necessarily limited to the mirror, and may be a material capable of reflecting light.

The probe tip mount 18 may be formed with a light gate 181. The light gate 181 may be formed at the center of the probe tip mount 18.

The reflective member 60 may reflect the light irradiated from the light projector 70 into the oral cavity through the light gate 181, and reflect the light reflected from the interior of the oral cavity to the camera lens 20 through the light gate 181.

A main mount 50 may be disposed in the main body 11. The main mount 50 may be mounted with the first camera lens 21, the second camera lens 22, and the light projector 70.

The front end of the first camera lens 21 may be disposed to be inclined toward the second camera lens 22, and the second camera lens 22 may be disposed to be inclined toward the first camera lens 21 so that the optical axis incident to the first camera lens 21 and the optical axis incident to the second camera lens 22 meet each other at the reflective member 60.

Further, the light projector 70 may be disposed inside the main body 11. The light projector 70 may be disposed between the first camera lens 21 and the second camera lens 22. The light projector 70 irradiates a predetermined emitted light between the first camera lens 21 and the second camera lens 22, and may irradiate the emitted light into the oral cavity through the opening 16 formed in the front end portion of the probe tip 14.

The intraoral scanner 1 according to an embodiment of the present disclosure proposes an optimal layout design, which may dispose the above-described configurations inside the case 10, seek the slim production of the main body 11 to easily grip and use the intraoral scanner 1 in terms of the user, and form the probe tip 14 as long and slim as possible to be easily inserted into and withdrawn from the oral cavity in terms of the dental patient.

Here, as described later, the slimming design of the main body 11 has the relationship with the layout design of the first imaging sensor 31b for sensing the incident light having passed through the first camera lens 21, and the second imaging sensor for sensing the incident light having passed through the second camera lens 22. Further, as described later, the slimming design of the probe tip 14 has the relationship with the layout design of the single polarization filter 80.

Hereinafter, the slimming design method of the main body 11 will be described in more detail.

The main mount 50 may have the front end portion of each of the first camera lens 21 and the second camera lens 22 to be protruded forward. The main mount 50 may have the rear end portion of each of the first camera lens 21 and the second camera lens 22 installed to be inserted therein.

Further, the main mount 50 may form a light waveguide tube, which is the path of the emitted light irradiated from the light projector 70 and the incident light incident to each of the first camera lens 21 and the second camera lens 22.

The light waveguide tube formed in the main mount 50 may be provided in the form of a dark room so that the incident light incident from the opening 16 and the emitted light irradiated from the light projector 70 are partitioned from each other not to affect each other.

That is, the light waveguide tube may include an emitted light path part 53 for providing the path of the emitted light irradiated from the light projector 70, a first incident light path part 51 for providing the path of the incident light incident through the first camera lens 21, and a second incident light path part 52 for providing the path of the incident light incident through the second camera lens 22.

The optical axis passing through each of the emitted light path part 53, the first incident light path part 51, and the second incident light path part 52 passes through a single polarization filter 80, as illustrated in FIG. 5. Therefore, the vibration waveform of the light passing through each of the emitted light path part 53, the first incident light path part 51, and the second incident light path part 52 may be represented in the same form.

Here, each of the emitted light path part 53, the first incident light path part 51, and the second incident light path part 52 may be provided to be partitioned from each other, thereby being provided so that the light of each path does not affect each other at all.

Further, since the light projector 70 is disposed between the first camera lens 21 and the second camera lens 22 that are disposed to be spaced at a predetermined distance apart from each other in the width direction of the main body 11, the emitted light path part 53 may be formed between the first incident light path part 51 and the second incident light path part 52.

The first incident light path part 51 may be formed to coincide with the longitudinal direction of the first camera lens 21 so that incident light incident from the first camera lens 21 is transmitted, and may be extended to be opened in one side surface of the main mount 50.

Further, the second incident light path part 52 may be formed to coincide with the longitudinal direction of the second camera lens 22 so that the incident light incident from the second camera lens 22 is transmitted, and may be extended to be opened in the other side surface of the main mount 50.

The first imaging board 31*a* may be vertically disposed so that both surfaces thereof are in close contact with one side surface of the main mount 50 and one side wall of the main body 11, respectively. At this time, the first imaging sensor 31*b* installed on the first imaging board 31*a* may be provided to be exposed to the first incident light path part 51.

Further, the second imaging board 32*a* may be vertically disposed so that both surfaces thereof may be in close contact with the other side surface of the main mount 50 and the other side wall of the main body 11, respectively. At this time, the second imaging sensor installed on the second imaging board 32*a* may be provided to be exposed to the second incident light path part 52.

Meanwhile, the intraoral scanner 1 according to an embodiment of the present disclosure may further include a first light path changing member 41 and a second light path changing member 42. The first light path changing member 41 may change the path of the light having passed through the first camera lens 21 through the first incident light path part 51 to the first imaging sensor 31*b*. The second light path changing member 42 may change the path of the light having passed through the second camera lens 22 through the second incident light path part 52 to the second imaging sensor.

The first light path changing member 41 and the second light path changing member 42 may be a mirror. However, the first light path changing member 41 and the second light path changing member 42 are not necessarily limited to the mirror, and may be any material capable of reflecting light.

A main technical gist of the intraoral scanner 1 according to an embodiment of the present disclosure is to secure three-dimensional video data of the internal figure of the patient's oral cavity (that is, an image) by using a pair of camera lenses 20.

However, as described above, the optical axis of each of the first camera lens 21 and the second camera lens 22 is disposed to meet each other at the reflective member 60, and the rear end portion of each of the first camera lens 21 and the second camera lens 22 may transmit the incident light having transmitted each of the first camera lens 21 and the second camera lens 22 in a straight-line direction.

Therefore, the first imaging board 31*a* should be disposed to be orthogonal to the rear end portion of the first camera lens 21, and the second imaging board 32*a* should be disposed to be orthogonal to the rear end portion of the second camera lens 22. However, in this case, there is the possibility of increasing the width-directional thickness of the main body 11 by the length of each of the first imaging board 31*a* and the second imaging board 32*a*.

However, as described above, the intraoral scanner 1 according to an embodiment of the present disclosure may form the incident light path parts 51, 52 to be opened to one side surface and the other side surface of the main mount 50, respectively, dispose the installation positions of the imaging boards 31*a*, 32*a* vertically between one side surface and the other side surface of the main mount 50 and one side wall and the other side wall of the case 10, and provide a pair of light path changing members 41, 42 for changing the path of the incident light having passed through the pair of camera lenses 20, thereby being slimly formed so that the measurer may easily grip and use the main body 11 only with the thumb, the index finger, and the middle finger.

The pair of light path changing members 41, 42 may be disposed to have a reflector surface of an angle at which the incident light having transmitted the pair of camera lenses 20 is incident perpendicular to one surface of each of the imaging sensors 31*b* provided on the pair of imaging boards 31*a*, 32*a*.

To this end, the pair of light path changing members 41, 42 may be disposed so that the reflector surface is inclined with respect to the longitudinal direction of the main body 11. That is, the first light path changing member 41 may be provided so that the incident light having transmitted the first camera lens 21 is incident through the first incident light path part 51 and then refracted by the reflector surface of the first light path changing member 41 to be irradiated to the first imaging sensor 31*b* of the first imaging board 31*a*. Likewise, the second light path changing member 42 may be provided so that the incident light having transmitted the second camera lens 22 is incident through the second incident light path part 52 and then refracted by the reflector surface of the second light path changing member 42 to be irradiated to the second imaging sensor of the second imaging board 32*a*.

Next, the sliming design method of the probe tip 14 will be described in more detail.

FIG. 7 is a schematic plane diagram for explaining the position design of a single polarization filter illustrated in FIGS. 4 to 6, and FIG. 8 is a schematic plane diagram illustrating a first angle of view, a second angle of view, and a triangulation angle illustrated in FIG. 7.

Referring to FIGS. 7 and 8, the light incident to the first camera lens 21 and the second camera lens 22 may overlap a predetermined length within the probe tip 14. The light projector 70 may be installed to emit light between the first camera lens 21 and the second camera lens 22.

The intraoral scanner 1 according to an embodiment of the present disclosure may further include the single polarization filter 80 for removing the internal reflected light of a measurement object 100 made of the internal reflective material such as teeth and passing through only the surface reflected light.

The single polarization filter 80 may be installed at the light gate 181 to be disposed within the probe tip mount 18. Ribs for coupling the single polarization filter 80 may be formed inside the probe tip mount 18, and a portion of the rim of the single polarization filter 80 may be fitted into and coupled to the ribs.

The single polarization filter 80 may be disposed between the light projector 70, the first camera lens 21, the second camera lens 22, and the opening 16. The single polarization filter 80 may be disposed to be spaced forward at a setting distance (d) apart from the light projector 70, the first camera lens 21, and the second camera lens 22.

The setting distance (d) may be a distance at which a first angle of view 91 irradiated from the light projector 70 into the oral cavity, and two second angles of view 92a, 92b reflected from the interior of the oral cavity to be incident to the first camera lens 21 and the second camera lens 22 do not overlap each other.

That is, the light emitted from the light projector 70 sequentially passes through the single polarization filter 80, the light gate 181, and the reflective member 60, and then is projected into the patient's oral cavity in which the measurement object 100 has been positioned through the opening 16, and here, the maximum area in which the light emitted from the light projector 70 has transmitted the single polarization filter 80 may be defined as the first angle of view 91, as described above.

Further, the light emitted from the light projector 70 to be projected into the patient's oral cavity flows into the probe tip 14 through the opening 16 again in the form of the reflected light reflected from the measurement object 100 and then sequentially passes through the reflective member 60, the light gate 181, and the single polarization filter 80 to be incident to each of the first camera lens 21 and the second camera lens 22, and at this time, the maximum area of the light having transmitted the single polarization filter 80 may be defined as the second angles of view 92a, 92b, as described above.

Here, if the position where the single polarization filter 80 has been installed is set to a position where the first angle of view 91 and the second angles of view 92a, 92b overlap each other, the light projected from the light projector 70 may be reflected from the transmitted surface of the single polarization filter 80 by itself to be incident to the first camera lens 21 and the second camera lens 22. In this case, the image obtained through the imaging sensors may generate a so-called ghost image, in which an image point brighter than the surrounding image is generated, or noise.

Therefore, the three-dimensional intraoral scanner 1 according to an embodiment of the present disclosure may be designed so that the setting distance (d) is set at the position where the first angle of view 91 and the second angles of view 92a, 92b forming while being transmitted through the single polarization filter 80 do not overlap each other, in order to block the above-described ghost image or noise from being generated in advance.

That is, the setting distance (d) defining the position of the single polarization filter 80 may be a distance at which the light projected from the light projector 70 into the oral cavity is not reflected from the single polarization filter 80 to the first camera lens 21 and the second camera lens 22.

Theoretically, since it is sufficient to set the setting distance (d) to position the single polarization filter 80 in a range where the first angle of view 91 and the second angles of view 92a, 92b do not overlap each other, the single polarization filter 80 may be positioned as close as possible to the front of the first camera lens 21 and the second camera lens 22. However, in this case, there is a problem that is contrary to the initial purpose for the slim production of the probe tip 14.

That is, in an embodiment of the present disclosure, in the case of applying the single camera lens 20, at least the size of the single polarization filter 80 is physically required to be larger than the sizes of the above-described first angle of view 91 and the second angle of view (see any one of reference numerals 92a, 92b in FIG. 7), such that it is expected that the width directional size thereof will increase inevitably if the single polarization filter 80 is designed to be positioned as close as possible to the front end of the single camera lens 20.

Further, in an embodiment of the present disclosure, in order to overcome the disadvantages raised when using the above-described single camera lens 20, in the case of applying the pair of camera lenses 20, the pair of camera lenses 20 is installed in the width direction of the main body 11, and the front end of the pair of camera lenses 20 is set to overlap each other by the probe tip 14. Here, since the single polarization filter 80 should be manufactured in the size at which at least the second angles of view 92a, 92b may be implemented, the width directional size of the single polarization filter 80 should be increased inevitably if the single polarization filter 80 has been designed as close as possible to the pair of camera lenses 20 side as described above, such that there occurs a problem of inhibiting the slim design of the probe tip 14.

In an embodiment of the three-dimensional intraoral scanner 1 according to the present disclosure, in order to solve the above-described problem, the setting distance (d) of the single polarization filter 80 may be set to a position where the size of the single polarization filter 80 is the smallest when assuming that the upper and lower widths and the left and right widths of the single polarization filter 80 (hereinafter, referred to as 'the size of the single polarization filter') increase as the single polarization filter 80 approaches toward the pair of camera lenses 20.

Further, the intraoral scanner 1 according to an embodiment of the present disclosure should set the single polarization filter 80 to a position free from the instrumental or structural interference between the single polarization filter 80 and the peripheral components even if the single polarization filter 80 approaches the pair of camera lenses 20 to have a minimum spacing distance.

To this end, the optimal setting distance (d) of the single polarization filter 80 may be set to satisfy the following equation, as illustrated in FIG. 8.

$$d < \frac{\left(l_i \ominus_i - \frac{D}{2}\right)}{2\tan a} + \frac{(l_p - l_i)}{2}$$ Equation where d refers to the setting distance, $l_p$ refers to the distance from the light projector to a measurement object, $l_t$ refers to the distance from the camera lens to the measurement object, $\ominus_i$ refers to the triangulation angle, D refers to the diameter of the camera lens, and a refers to the angle of view of the light irradiated from the light projector. The measurement object is located at the same position as the focal plane (FP as illustrated in FIG. 7 and FIG. 8).

According to the equation, the smaller the setting distance (d) is, the better it is, such that the single polarization filter 80 may be positioned close to the minimum distance as long as the instrumental interference with the pair of camera lenses 20 does not occur. However, as described above, since there is a problem in that the overall size increases if the single polarization filter 80 is close to the pair of camera lenses 20, the design should be done considering the purpose of the slim production in an embodiment of the present disclosure even in this case.

Here, referring to FIG. 8, the D refers to the diameter of the first camera lens 21, and an increase in the D means that the setting distance (d) should be designed to be smaller and becomes an obstacle to the slimming design. Therefore, it is preferable to design the D to be as minimized as possible, and the light projector 70 and each of the pair of camera lenses 21, 22 should prioritize an optima structure design in which the instrumental interference does not occur.

Further, as illustrated in FIG. 8, the intraoral scanner 1 according to an embodiment of the present disclosure should satisfy the condition where the reflected light should not be transmitted directly to the first camera lens 21 through the single polarization filter 80 forming the first angle of view 91. Here, an increase in the diameter (D) of the first camera lens 21 leads to an increase in the second angle of view 92b, and in this case, since the first angle of view 91 and the second angle of view 92b may overlap each other, the setting distance (d) should be designed to be smaller.

The equation suggests a theoretical background for deriving an optimal setting distance (d) of the single polarization filter 80 capable of implementing all of these purposes.

Meanwhile, the opening 16 formed in the probe tip 14 may be provided with the reflective member 60 as described above. The reflective member 60 serves to reflect the incident light incident into the main body 11 and the emitted light emitted from the interior of the main body 11 to a certain path. The reflective member 60 may be provided in the form of a mirror or a prism.

In particular, the reflective member 60 irradiates the light irradiated by the light projector 70 into the oral cavity through the opening 16 formed to be opened in the direction orthogonal to the longitudinal direction of the probe tip 14 and also reflects the light reflected from the interior of the oral cavity to the pair of camera lenses 20, thereby facilitating the operation of scanning the interior of the oral cavity.

Here, the single polarization filter 80 may be positioned between the pair of camera lenses 20 and the reflective member 60, disposed at the front of the light projector 70 and the pair of camera lenses 20, and disposed in parallel with the front surface of the light projector 70. The meaning that the single polarization filter 80 is disposed in parallel with the front surface of the light projector 70 means that each polarization filter is provided for each emitted path of the emitted light from the conventional light projector 70 and the incident path of the incident light to the camera lens, and there has the advantage capable of deleting the complicated process of designing the position of each polarization filter very precisely in order to lower the polarization efficiency.

An operation of the intraoral scanner 1 according to an embodiment of the present disclosure configured as described above will be described in detail with reference to the accompanying drawings (in particular, FIGS. 4 to 7) as follows.

The operator operates the user input part 15 provided on the upper portion of the main body 11 to make a measurement by using the intraoral scanner 1 into the patient's oral cavity.

Then, as illustrated in FIGS. 5 and 8, the emitted light is irradiated from the light projector 70. The emitted light irradiated from the light projector 70 sequentially passes through the emitted light path part 53 formed in the main mount 50, the single polarization filter 80, the light gate 181 formed in the probe tip mount 18, and the internal space of the probe tip 14, and then is irradiated into the patient's oral cavity through the opening 16 by the reflective member 60.

At the same time, as illustrated in FIGS. 5 and 7, a pair of camera lenses 20 may be operated by an operation of the user input part 15 operated by the operator, thereby securing two image data using any one point of the image as the same focal point.

At this time, the image of the patient's oral cavity is present in the form of light by the emitted light, and, in contrast to the emitted light, is reflected from a structure (teeth and gum) in the oral cavity to be incident into the probe tip 14 through the opening 16, and then sequentially passes through the reflective member 60, the internal space of the probe tip 14, the light gate 181, and the single polarization filter 80 to be incident to the pair of camera lenses 21, 22, respectively, and the incident light having passed through the pair of camera lenses 21, 22, respectively may be irradiated to the imaging sensor of the corresponding imaging boards 31a, 32a by each of the light path changing members 41, 42 via the incident light path parts 51, 52, thereby securing two predetermined image data at the same time. It is possible to easily secure the three-dimensional data on the image of the patient's oral cavity based on the two image data thus secured.

FIGS. 9 to 12 are diagrams for explaining the advantages of a single polarization filter.

Referring to FIG. 9A, it may be assumed that the single polarization filter 80 is not provided inside the intraoral scanner 1, and a plurality of polarization filters 81, 82, 83 are provided. That is, the first polarization filter 81 is provided in front of the first camera lens 21, the second polarization filter 82 is provided in front of the light projector 70, and the third polarization filter 83 may be provided in front of the second camera lens 22.

In this case, when the first polarization filter 81, the second polarization filter 82, and the third polarization filter 83 are installed inside the intraoral scanner 1, fixing parts should be prepared on at least two points for each of the polarization filters 81, 82, 83 in order to fix the polarization filters 81, 82, 83.

That is, a first fixing part (F1) and a second fixing part (F2) should be prepared in the first polarization filter 81, a third fixing part (F3) and a fourth fixing part (F4) should be prepared in the second polarization filter 82, and a fifth fixing part (F5) and a sixth fixing part (F6) should be prepared in the third polarization filter 83.

As described above, if three polarization filters 81, 82, 83 are provided instead of the single polarization filter 80, six man-hours occur at the points of the fixing parts (F1 to F6) when installing the polarization filters 81, 82, 83.

However, referring to FIG. 9B, in the intraoral scanner 1 according to an embodiment of the present disclosure, since the single polarization filter 80 is provided at the position spaced at the setting distance (d) apart from the front of the light projector 70, the first camera lens 21, and the second camera lens 22, only the first fixing part (F1) and the second fixing part (F2) are prepared in the single polarization filter 80.

Therefore, since only two man-hours occur at the points of the fixing parts (F1, F2) when installing the single polarization filter 80, it is possible to quickly install the single polarization filter 80. Further, since the instrumental structure inside the intraoral scanner 1 is reduced, a tolerance in the instrument development process may also be reduced.

Further, referring to FIG. 10A, if the three polarization filters 81, 82, 83 are provided, the apex of each of the polarization filters 81, 82, 83 ideally has the same Y coordinate value on the X-Y coordinates.

That is, it is ideal that the Y coordinate values of a, a' and a" should be the same, the Y coordinate values of b, b' and b" should be the same, the Y coordinate values of c, c' and c" should be the same, and the Y coordinate values of d, d' and d" should be the same.

However, if the Y coordinate value of the apex of each of the polarization filter 81, 82, 83 is not the same, at least the angles of the line ac, the line a'c' and the line a"c" should be the same.

However, referring to FIG. 10B, since the intraoral scanner 1 according to an embodiment of the present disclosure is provided as the single polarization filter 80, it is sufficient that the X coordinate values of a and c are the same, the X coordinate values of b and d are the same, the Y coordinate values of a and b are the same, and the Y coordinate values of c and d are the same.

Therefore, if the single polarization filter 80 is provided, calculation of the instrumental design for adjusting the positions of a, b, c, d is easier than the case provided as the three polarization filters 81, 82, 83.

Referring to FIG. 11A, light is an electromagnetic wave, and an electric field and a magnetic field vibrate in the directions (B, E) perpendicular to the progressing direction (Z). The polarization of light is classified according to the vibration direction of the electric field. That is, the wave of light is composed of an S wave (S WAVE) vibrating in the direction perpendicular to the incident surface and a P wave (P WAVE) vibrating in the direction horizontal to the incident surface.

Referring to FIG. 11B, the light projector 70 may include a projection engine 70a for generating light of a predetermined pattern, and a projection lens 70b for transmitting the light irradiated from the projection engine 70a.

The projection engine 70a may generate coded structured light along a projection path to project it onto the projection lens 70b. The light projected from the light projector 70 may include the S wave and the P wave.

The light projected from the light projector 70 passes through the single polarization filter 80 to remove the S wave, and becomes the polarization state where only the P wave remains. Here, although the single polarization filter 80 has been illustrated as removing the S wave, the single polarization filter 80 may also remove the P wave. That is, the single polarization filter 80 may filter any one of the S wave and the P wave, and pass through the other. In the following description, it will be described that the single polarization filter 80 is limited to removing the S wave and passing through the P wave.

The P wave having passed through the single polarization filter 80 may be reflected from the surface of the teeth, which is the measurement object 100, to maintain the polarization state, but may be projected into the teeth to add the S wave, which is noise. Therefore, the light reflected from the measurement object 100 to the single polarization filter 80 includes the S wave and the P wave, and the single polarization filter 80 removes the S wave, which is the noise, from the light reflected from the teeth and passes through the P wave.

Thereafter, the P wave having passed through the single polarization filter 80 may sequentially pass through the camera lens 21 and the light path changing member 41 and then may be incident to the imaging sensor 31b, thereby obtaining the accurate image data.

Further, referring to FIGS. 12A to 12D, if three polarization filters 81, 82, 83 are provided, an assembly tolerance may occur inevitably when installing the intraoral scanner 1 therein. FIG. 12A illustrates that a tolerance has occurred in the third polarization filter 83, FIG. 12B illustrates that a tolerance has occurred in the first polarization filter 81, FIG. 12C illustrates that a tolerance has occurred in the second polarization filter 82, and FIG. 12D illustrates that a tolerance has occurred in the first polarization filter 81 and the third polarization filter 83. Further, although not illustrated in the drawings, a tolerance may also occur in the first polarization filter 81 and the second polarization filter 82, and a tolerance may also occur in the second polarization filter 82 and the third polarization filter 83, and a tolerance may also occur in all of the first polarization filter 81, the second polarization filter 82, and the third polarization filter 83.

As the number of the polarization filters 81, 82, 83 increases, the precision of the measured value according to the tolerance of each of the polarization filters 81, 82, 83 are significantly lowered. That is, assuming that the accuracy of the measured value is 100% if two polarization filters are provided, the precision of the measured values in the five polarization filters is inevitably lower than 100%.

As the number of the camera lenses 20 increases, the efficiency of the incident light relative to the projection light lowers according to the tolerances of each of the polarization filters 81, 82, 83 and the amount of light reflected from the interior of the object may not be filtered accurately to affect precision.

That is, if the efficiency of the incident light relative to the projection light passing through the single polarization filter having the same polarization angle is '$\eta_p$', the efficiency of the case where the tolerance occurs at the angle of '$\theta$' in at least one among the first polarization filter 81, the second polarization filter 82, and the third polarization filter 83 may be represented as $\eta=\eta_p \times \cos\theta$.

However, referring to FIG. 12E, since the intraoral scanner 1 according to an embodiment of the present disclosure is provided as the single polarization filter 80, a tolerance occurs when installing the single polarization filter 80, and therefore, even if the Y coordinate values of a and b are different, in the single polarization filter 80, the angle of a first area (S1) corresponding to any one 92a of the second angles of view 92a, 92b, the angle of a second area (S2) corresponding to the first angle of view 91, and the angle of a third area (S3) corresponding to the other one 92b of the second angles of view 92a, 92b are the same, such that the efficiency of the light irradiated from the light projector 70 and the efficiency of the light incident to the first camera lens 21 and the second camera lens 22 are the same.

In this case, since the first angle of view 91 and the second angles of view 92a, 92b are adjusted in size by the equation, there is no deviation from the single polarization filter 80.

FIG. 13 is a diagram illustrating the moving path of the air sucked into the intraoral scanner according to an embodiment of the present disclosure, FIG. 14 is an enlarged diagram of the probe tip mount illustrated in FIG. 3, and FIG. 15 is a diagram illustrating a back cover installed at the rear of the main body.

Referring to FIGS. 13 to 15, the intake fan 30 may be further disposed inside the main body 11. A control board for controlling the on/off of the intake fan 30 may be further installed inside the main body 11.

The intake fan 30 may suck the outside air into the main body 11 at the rear of the main body 11 at operation. The air outside the main body 11 may flow into the main body 11 by the operation of the intake fan 30. The air flowing into the main body 11 by the operation of the intake fan 30 may be heated by the heat generated in the electrical component in the main body 11.

The probe tip mount 18 may be made of a heat dissipation material in order to easily discharge the heat in the main body 11 to the outside of the main body 11. The heat dissipation material is preferably an aluminum material. However, the heat dissipation material is not limited to the aluminum material, but may also be made of another material having the function of heat dissipation.

The probe tip mount 18 may dissipate the heat generated from the main mount 50 to the outside. To this end, the rear end portion of the probe tip mount 18 is preferably disposed in contact with the front end portion of the main mount 50.

The probe tip mount 18 may be further formed with guide holes (H1, H2) for guiding the air flowing into the main body 11 by the intake fan 30 to the reflective member 60.

The outside air sucked into the main body 11 at operation of the intake fan 30 may be heated by the heat generated from the electrical component in the main body 11. Further, some of the heated air in the main body 11 may be moved to the reflective member 60 through the guide holes (H1, H2). Therefore, when the patient's oral cavity is scanned by inserting the front end portion of the probe tip 14 therein, the condensation phenomenon of the reflective member 60 may be prevented by the water vapor in the oral cavity.

The guide holes (H1, H2) may be formed to be recessed in the outer circumferential surface of the probe tip mount 18. That is, the guide holes (H1, H2) may be formed so that the outer circumferential surface direction and the front and rear direction of the probe tip mount 18 are opened.

The guide holes (H1, H2) may include the first guide hole (H1) and the second guide hole (H2). The first guide hole (H1) may be formed at one side of the outer circumferential surface of the probe tip mount 18. The second guide hole (H2) may be formed at the other side of the outer circumferential surface of the probe tip mount 18.

In this embodiment, although the first guide hole (H1) has been formed in the upper side of the outer circumferential surface of the probe tip mount 18 and the second guide hole (H2) is formed in the lower side of the outer circumferential surface of the probe tip mount 18, the first guide hole (H1) may be formed in the left side of the outer circumferential surface of the probe tip mount 18, and the second guide hole (H2) may be formed in the right side of the outer circumferential surface of the probe tip mount 18. Further, the guide holes (H1, H2) may also be formed in the entire outer circumferential surface of the probe tip mount 18. Further, the guide holes (H1, H2) may also be formed in the outside of the interior of the probe tip mount 18 from the light gate 181 to communicate back and forth.

The probe tip mount 18 may be further formed with a plurality of first partition walls 183 and a plurality of second partition walls 185. The plurality of first partition walls 183 may partition the first guide hole (H1) into a plurality of first guide holes (H1). The plurality of second partition walls 185 may partition the second guide hole (H2) into a plurality of second guide holes (H2).

The plurality of first partition walls 183 and the plurality of second partition walls 185 may increase the heat exchange by increasing the contact area with the outside air, thereby further enhancing heat dissipation performance inside the main body 11.

It is possible to increase or decrease the number of the plurality of partition walls 183, 185, or to increase or decrease the surface areas of the plurality of partition walls 183, 185 to change the surface area thereof, thereby adjusting the amount of the heated air that is present inside the main body 11 by the plurality of partition walls 183, 185. In particular, in the case of increasing the number or the surface area of the plurality of partition walls 183, 185, the area contacting the outside increases, such that it is possible to increase the amount of the heat exchange between the air outside the probe tip mount 18 and the air inside the main body 11. Therefore, it is possible to well discharge the heat generated from the optical elements to the outside, thereby reducing the phenomenon that the light projector 70 and the camera lens 20 may be distorted by the heat. Therefore, it is possible to help to secure accurate three-dimensional scan data.

The guide holes (H1, H2) may be formed in the upper side of the outer circumferential surface of the probe tip mount 18 and in the lower side of the outer circumferential surface of the probe tip mount 18, respectively, thereby moving only a portion of air to the reflective member 60.

This is for preventing discomfort thereby because the accurate scan data may be secured by drying the teeth-stained saliva if a large amount of heated air entirely moves toward the reflective member 60 but the interior of the subject's oral cavity becomes too dry.

The back cover 90 may be installed at the rear of the main body 11. The main body 11 may have the front end and the rear end opened, the opened front end of the main body 11 may be installed so that the probe tip mount 18 is protruded forward, and the back cover 90 may be installed at the opened rear end of the main body 11.

The back cover 90 may be installed to be inserted into the opened rear end of the main body 11. The back cover 90 may be disposed at the rear of the intake fan 30 to face the intake fan 30. A power cable (C) may penetrate the back cover 90.

An intake port 90*a* may be formed on the back cover 90. The intake port 90*a* may be formed in a circular shape at the center of the back cover 90.

A guide member 95 may be coupled to the inside of the back cover 90. The guide member 95 may partition the intake port 90*a* into a plurality of passages. In this embodiment, although the guide member 95 has been illustrated as partitioning the intake port 90*a* into three passages, the number of the partitions of the intake port 90*a* may be changed variously.

Air discharge holes (H3, H4) may be formed in the rim of the back cover 90. The air discharge holes (H3, H4) may discharge the air flowing into the main body 11 through the intake port 90*a*.

That is, the outside air sucked into the main body 11 may be heated by exchanging heat with the electrical component in the main body 11 by the operation of the intake fan 30. A portion of the heated air may be moved to the reflective member 60 through the guide holes (H1, H2), and the remainder of the heated air may be discharged to the outside of the main body 11 through the air discharge holes (H3, H4).

The air discharge holes (H3, H4) may be positioned to correspond to portions of the outer circumferential surface of the probe tip mount 18 where the guide holes (H1, H2) are not formed. Therefore, a portion of the heated air in the main body 11 may move to the reflective member 60 through the guide holes (H1, H2), and the remainder of the heated air may hit the rear surface of the probe tip mount 18 to flow backward and may be easily discharged through the air discharge holes (H3, H4).

The air discharge holes (H3, H4) may include the first air discharge hole (H3) and the second air discharge hole (H4).

The first air discharge hole (H3) may be formed in one side of the rim of the back cover 90. The second air discharge hole (H4) may be formed in the other side of the rim of the back cover 90.

That is, the first air discharge hole (H3) may be formed in the left side of the rim of the back cover 90, and the second air discharge hole (H4) may be formed in the right side of the rim of the back cover 90. Alternatively, the first air discharge hole (H3) may also be formed in the upper side of the rim of the back cover 90, and the second air discharge hole (H4) may also be formed in the lower side of the rim of the back cover 90. Alternatively, the air discharge holes (H3, H4) may also be formed in the entire rim of the back cover 90.

As described above, in the intraoral scanner 1 according to an embodiment of the present disclosure, since the guide holes (H1, H2) for guiding the air flowing into the main body 11 by the intake fan 30 to the reflective member 60 are formed in the probe tip mount 18, a portion of the heated air in the main body 11 may be moved to the reflective member 60 through the guide holes (H1, H2), thereby preventing the condensation phenomenon of the reflective member 60.

Further, since the air discharge holes (H3, H4) through which the remainder of the heated air is discharged are formed in the rim of the back cover 90, the remainder of the heated air may be discharged through the air discharge holes (H3, H4).

Further, since the air discharge holes (H3, H4) are positioned to correspond to portions of the outer circumferential surface of the probe tip mount 18 where the guide holes (H1, H2) are not formed, a portion of the heated air may be moved to the reflective member 60 through the guide holes (H1, H2), and the remainder of the heated air may hit the rear surface of the probe tip mount 18 and then may be moved backward, at operation of the intake fan 30 disposed inside the main body 11, thereby smoothly discharging it through the air discharge holes (H3, H4).

Further, since the single polarization filter 80 is disposed at the front of the camera lens 20, the light transmitted to and then reflected from the interior of the teeth may be removed from the light reflected from the interior of the oral cavity to be incident into the intraoral scanner, thereby securing the accurate image data.

Those skilled in the art to which the present disclosure pertains will appreciate that the present disclosure may be embodied in other specific forms without changing the technical spirit or essential features thereof. Therefore, it should be understood that the embodiments described above are exemplary in all respects and not restrictive. The scope of the present disclosure is indicated by the following claims rather than the above description, and it should be construed that all changes or modified forms derived from the meaning and scope of the claims and their equivalents are included in the scope of the present disclosure.

What is claimed is:

1. An intraoral scanner, comprising:
a main body having a light projector, a camera lens, and an intake fan disposed therein, wherein the intake fan is configured to suck an air from an outside of the main body into the main body such that the air sucked into the main body are heated by a heat inside the main body;
a probe tip mount disposed at the front end of the main body, and formed with a light gate; and
a probe tip having a rear end portion into which the probe tip mount is inserted, and having a front end portion on which a reflective member is disposed for reflecting the light irradiated from the light projector through the light gate into an oral cavity and reflecting the light reflected from the interior of the oral cavity to the camera lens through the light gate,
wherein the probe tip mount is further formed with a guide hole for guiding the air flowing into the main body by the intake fan and heated inside the main body to the reflective member such that the air flowing onto the reflective member disposed on the front end portion of the probe tip prevents condensation phenomenon on the reflective member,
wherein the probe tip mount further comprises a single polarization filter that is installed inside the probe tip mount to be disposed at the light gate,
wherein the single polarization filter is disposed to be spaced forward at a setting distance apart from the light projector and the camera lens, and
wherein the setting distance satisfies the following equation:

$$d < \frac{\left(l_i \ominus_i - \frac{D}{2}\right)}{2\tan\alpha} + \frac{(l_p - l_i)}{2},$$

where d refers to the setting distance, $l_p$ refers to the distance from the light projector to a measurement object, $l_i$ refers to the distance from the camera lens to the measurement object, $\ominus_t$ refers to the triangulation angle, D refers to the diameter of the camera lens, and α refers to the angle of view of the light irradiated from the light projector.

2. The intraoral scanner of claim 1, wherein the guide hole is formed to be recessed in the outer circumferential surface of the probe tip mount.

3. The intraoral scanner of claim 2, wherein the guide hole comprises
a first guide hole formed in one side of the outer circumferential surface of the probe tip mount; and
a second guide hole formed in the other side of the outer circumferential surface of the probe tip mount.

4. The intraoral scanner of claim 3, wherein the probe tip mount further comprises
a plurality of first partition walls for partitioning the first guide hole into a plurality of first guide holes; and
a plurality of second partition walls for partitioning the second guide hole into a plurality of second guide holes.

5. The intraoral scanner of claim 1, wherein the probe tip mount is made of a heat dissipation material.

6. The intraoral scanner of claim 1, wherein the camera lens is provided as a plurality of camera lenses.

7. An intraoral scanner, comprising:
a main body having a light projector, a camera lens, and an intake fan disposed therein;
a probe tip mount disposed at the front end of the main body, and formed with a light gate; and
a probe tip having the probe tip mount inserted into the rear end portion thereof, and having a reflective member for reflecting the light irradiated from the light projector through the light gate into an oral cavity and reflecting the light reflected from the interior of the oral cavity to the camera lens through the light gate disposed on the front end portion thereof,
wherein the probe tip mount is further formed with a guide hole for guiding the air flowing into the main body by the intake fan to the reflective member, wherein the intraoral scanner further comprises a back cover disposed at the rear of the main body, and formed with an intake port, and wherein the rim of the back cover is formed with an air discharge hole for discharging the air flowing into the main body through the intake port, wherein the probe tip mount further comprises a single polarization filter that is installed inside the probe tip mount to be disposed at the light gate, wherein the single polarization filter is disposed to be spaced forward at a setting distance apart from the light projector and the camera lens, and wherein the setting distance satisfies the following equation:

$$d < \frac{\left(l_i \Theta_t - \frac{D}{2}\right)}{2\tan\alpha} + \frac{(l_p - l_i)}{2},$$

where d refers to the setting distance, $l_p$ refers to the distance from the light projector to a measurement object, $l_i$ refers to the distance from the camera lens to the measurement object, $\Theta_t$ refers to the triangulation angle, D refers to the diameter of the camera lens, and $\alpha$ refers to the angle of view of the light irradiated from the light projector.

8. The intraoral scanner of claim 7, wherein the air discharge hole comprises a first air discharge hole formed in one side of the rim of the back cover; and a second air discharge hole formed in the other side of the rim of the back cover.

9. An intraoral scanner, comprising:

a main body having a light projector, a camera lens, and an intake fan disposed therein;

a probe tip mount disposed at the front end of the main body, and formed with a light gate; and a probe tip having the probe tip mount inserted into the rear end portion thereof, and having a reflective member for reflecting the light irradiated from the light projector through the light gate into an oral cavity and reflecting the light reflected from the interior of the oral cavity to the camera lens through the light gate disposed on the front end portion thereof, wherein the probe tip mount is further formed with a guide hole for guiding the air flowing into the main body by the intake fan to the reflective member, wherein the camera lens is provided as a plurality of camera lenses, and wherein the intraoral scanner further comprises a main mount disposed in the main body, and having the plurality of camera lenses and the light projector mounted thereon, wherein the main mount is formed with a plurality of incident light path part for providing the path of the light incident to the plurality of camera lenses, and an emitted light path part for providing the path of the light irradiated from the light projector, wherein the probe tip mount further comprises a single polarization filter that is installed inside the probe tip mount to be disposed at the light gate, wherein the single polarization filter is disposed to be spaced forward at a setting distance apart from the light projector and the camera lens, and wherein the setting distance satisfies the following equation:

$$d < \frac{\left(l_i \Theta_t - \frac{D}{2}\right)}{2\tan\alpha} + \frac{(l_p - l_i)}{2},$$

where d refers to the setting distance, $l_p$ refers to the distance from the light projector to a measurement object, $l_i$ refers to the distance from the camera lens to the measurement object, $\Theta_t$ refers to the triangulation angle, D refers to the diameter of the camera lens, and $\alpha$ refers to the angle of view of the light irradiated from the light projector.

10. The intraoral scanner of claim 9, wherein the probe tip mount dissipates the heat generated in the main mount to the outside.

\* \* \* \* \*